United States Patent
Pressman et al.

(10) Patent No.: US 6,800,779 B2
(45) Date of Patent: Oct. 5, 2004

(54) METHOD FOR PRODUCING AROMATIC CARBONATES

(75) Inventors: Eric James Pressman, East Greenbush, NY (US); John Yaw Ofori, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 09/822,531

(22) Filed: Mar. 30, 2001

(65) Prior Publication Data

US 2002/0177724 A1 Nov. 28, 2002

(51) Int. Cl.$^7$ .................................. C07C 68/04
(52) U.S. Cl. ............................................ 558/274
(58) Field of Search ......................... 558/274

(56) References Cited

U.S. PATENT DOCUMENTS

| | | | |
|---|---|---|---|
| 4,187,242 A | 2/1980 | Chalk | |
| 5,231,210 A | 7/1993 | Joyce et al. | |
| 5,239,106 A | 8/1993 | Shafer | |
| 5,284,964 A | 2/1994 | Pressman et al. | |
| 5,373,083 A | 12/1994 | King et al. | |
| 5,380,907 A | 1/1995 | Mizukami et al. | |
| 5,399,734 A | 3/1995 | King et al. | |
| 5,498,742 A | 3/1996 | Buysch et al. | |
| 5,498,789 A | 3/1996 | Takagi et al. | |
| 5,502,232 A | 3/1996 | Buysch et al. | |
| 5,543,547 A | 8/1996 | Iwane et al. | |
| 5,625,091 A | 4/1997 | Buysch et al. | |
| 5,726,340 A | 3/1998 | Takagi et al. | |
| 5,760,272 A | 6/1998 | Pressman et al. | |
| 5,821,377 A | 10/1998 | Buysch et al. | |
| 5,856,554 A | 1/1999 | Buysch et al. | |
| 5,917,078 A | 6/1999 | Battista et al. | |
| 6,114,564 A | 9/2000 | Pressman et al. | |
| 6,172,254 B1 | 1/2001 | Pressman et al. | |
| 6,180,812 B1 | 1/2001 | Johnson et al. | |
| 6,191,299 B1 | 2/2001 | Pressman et al. | |
| 6,197,991 B1 | 3/2001 | Spivack et al. | |

FOREIGN PATENT DOCUMENTS

| | | |
|---|---|---|
| EP | 736325 | 3/1996 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |
| JP | 98-158221 | 6/1998 |
| WO | WO-00/37419 A1 * | 6/2000 |

* cited by examiner

Primary Examiner—Laura L. Stockton
(74) Attorney, Agent, or Firm—Andrew J. Caruso; Patrick K. Patnode

(57) ABSTRACT

A method for economically producing aromatic carbonates from aromatic hydroxy compounds is disclosed which in one embodiment comprises the steps of: (i) contacting at a temperature sufficient to keep the mixture molten at least one aromatic hydroxy compound with a catalyst composition comprising the following and any reaction products thereof: (A) at least one Group 8, 9, or 10 metal or a compound thereof; (B) at least one salt; (C) at least one metal co-catalyst; and (D) optionally, at least one activating solvent; (ii) optionally heating the mixture at atmospheric pressure to a temperature above that sufficient to keep the mixture molten; (iii) pressurizing the mixture with carbon monoxide; (iv) optionally heating the mixture under pressure of carbon monoxide to a temperature above that sufficient to keep the mixture molten; (v) optionally maintaining the mixture under pressure of carbon monoxide for a time period; (vi) introducing oxygen to the mixture to a desired concentration of oxygen in carbon monoxide; (vii) starting gas flow to the mixture at a desired concentration of oxygen and carbon monoxide; (viii) optionally maintaining gas flow for a time period at less than a desired ultimate temperature for the mixture; and (ix) optionally heating the mixture to a desired ultimate temperature under flow of gases.

3 Claims, No Drawings

METHOD FOR PRODUCING AROMATIC CARBONATES

BACKGROUND OF THE INVENTION

The present invention is directed to a method for producing aromatic carbonates and, more specifically, to a method for producing diaryl carbonates through the carbonylation of aromatic hydroxy compounds.

Aromatic carbonates find utility, inter alia, as intermediates in the preparation of polycarbonates. For example, a popular method of polycarbonate preparation is the melt transesterification of aromatic carbonates with bisphenols.

Various methods for preparing aromatic carbonates have been previously described in the literature and/or utilized by industry. A method that has enjoyed substantial popularity in the literature involves the direct carbonylation of aromatic hydroxy compounds with carbon monoxide and oxygen catalyzed by at least one Group 8, 9, or 10 metal source. Further refinements to the carbonylation catalyst composition include the identification of co-catalysts.

The utility of the carbonylation process is strongly dependent on the number of moles of aromatic carbonate produced per mole of Group 8, 9, or 10 metal utilized (i.e. "catalyst turnover number or "TON""). Consequently, much work has been directed to the identification of efficacious process variations that increase catalyst turnover and yield of aromatic carbonate.

As the demand for high performance plastics has continued to grow, still new and improved methods of providing product more economically are needed to supply the market. In this context, various processes and catalyst systems are constantly being evaluated; however, the identities of improved and/or additional effective catalyst systems for these processes continue to elude the industry. Consequently, a long felt, yet unsatisfied need exists for new and improved methods and catalyst systems for producing aromatic carbonates and the like.

The start-up procedure for the carbonylation process is an important step in the overall process. More particularly, an incorrect start-up procedure can result in rapid catalyst inactivation and render a carbonylation catalyst system ineffective for producing high yields of aromatic carbonate. A consistently effective start-up procedure for a carbonylation reaction is a long-felt need in the art.

SUMMARY OF THE INVENTION

After diligent experimentation the present inventors have discovered a method for producing aromatic carbonates which comprises an effective start-up procedure. Thus, in one embodiment, the present invention provides a method for producing aromatic carbonates which comprises the steps of:

(i) contacting at a temperature sufficient to keep the mixture molten at least one aromatic hydroxy compound with a catalyst composition comprising the following and any reaction products thereof:
   (A) at least one Group 8, 9, or 10 metal or a compound thereof;
   (B) at least one salt;
   (C) at least one metal co-catalyst; and
   (D) optionally, at least one activating solvent;

(ii) optionally heating the mixture at atmospheric pressure to a temperature above that sufficient to keep the mixture molten;

(iii) pressurizing the mixture with carbon monoxide;

(iv) optionally heating the mixture under pressure of carbon monoxide to a temperature above that sufficient to keep the mixture molten;

(v) optionally maintaining the mixture under pressure of carbon monoxide for a time period;

(vi) introducing oxygen to the mixture to a desired concentration of oxygen in carbon monoxide;

(vii) starting gas flow to the mixture at a desired concentration of oxygen and carbon monoxide;

(viii) optionally maintaining gas flow for a time period at less than a desired ultimate temperature for the mixture; and (ix) optionally heating the mixture to a desired ultimate temperature under flow of gases.

In another embodiment, the invention provides a method for producing aromatic carbonate from a mixture comprising an aromatic hydroxy compound, which comprises the steps of:

(x) maintaining the mixture at a temperature at least sufficient to keep the mixture molten;

(xi) introducing oxygen and carbon monoxide to the mixture to a desired pressure;

(xii) starting gas flow to the mixture at a desired concentration of oxygen and carbon monoxide;

(xiii) heating the mixture to a temperature in a range between that sufficient to keep the mixture molten and a desired ultimate temperature; and (xiv) contacting the mixture with one or more mixtures comprising aromatic hydroxy compound and one or more catalyst components comprising the following and any reaction products thereof:
   (A) at least one Group 8, 9, or 10 metal or a compound thereof;
   (B) at least one salt;
   (C) at least one metal co-catalyst; and
   (D) optionally, at least one activating solvent.

Various other features, aspects, and advantages of the present invention will become more apparent with reference to the following description and appended claims.

DETAILED DESCRIPTION OF THE INVENTION

Unless otherwise noted, the term "effective amount," as used herein, includes that amount of a substance capable of either increasing (directly or indirectly) the yield of the carbonylation product or increasing selectivity toward an aromatic carbonate. Effective amounts of a given substance can vary based on reaction conditions and the identity of other constituents yet can be readily determined in light of the discrete circumstances of a given application.

Any aromatic hydroxy compound convertible to a carbonate ester may be employed in the present invention. Suitable aromatic hydroxy compounds include monocyclic, polycyclic or fused polycyclic aromatic monohydroxy or polyhydroxy compounds having from 6 to 30, and preferably from 6 to 15 carbon atoms. Illustrative examples include mono- and poly-hydroxy compounds such as phenol, alkylphenols, o-, m- or p-cresol, o-, m- or p-chlorophenol, o-, m- or p-ethylphenol, o-, m- or p-propylphenol, o-, m- or p-methoxyphenol, methyl salicylate, 2,6-dimethylphenol, 2,4-dimethylphenol, 3,4-dimethylphenol, 1-naphthol and 2-naphthol, xylenol, resorcinol, hydroquinone, catechol, cumenol, the various isomers of dihydroxynaphthalene, bis(4-hydroxyphenyl)

propane-2,2,αα'-bis(4-hydroxyphenyl)-p-diisopropylbenzene, and bisphenol A. Aromatic monohydroxy compounds are particularly preferred with phenol being the most preferred. In the case of substituents on the aromatic hydroxy compound, the substituents are generally 1 or 2 substituents and are preferably from C-1 to C-4 alkyl, C-1 to C-4 alkoxy, fluorine, chlorine or bromine.

When an aromatic hydroxy compound as a raw material is used as a reaction solvent, then another solvent need not be used. However, the mixture may also optionally contain at least one relatively inert solvent, that is a solvent whose presence does not substantially improve the yield of or selectivity toward the aromatic carbonate. Illustrative inert solvents include, but are not limited to, hexane, heptane, cyclohexane, methylene chloride, or chloroform, or an aromatic solvent such as toluene or xylene.

In various preferred embodiments, the carbonylation catalyst system contains at least one constituent from the Group 8, 9, or 10 metals or a compound thereof. A preferred Group 8, 9, or 10 metal constituent is one having an atomic number of at least 44. A particularly preferred Group 8, 9, or 10 metal constituent is an effective amount of a palladium source. In various embodiments, the palladium source may be in elemental form, or it may be employed as a palladium compound. The palladium source can be employed in a form that is substantially soluble in the reaction media or that becomes substantially soluble in the reaction mixture, or in a form which is substantially insoluble in the reaction media, such as a supported- or polymer-bound palladium source. Accordingly, palladium black or palladium deposited on carbon, palladium deposited on alumina or palladium deposited on silica may be used as well as palladium halides, palladium chloride, palladium bromide, palladium iodide; palladium sulfate; palladium nitrate, palladium carboxylates, palladium oxides, palladium acetate and palladium 2,4-pentanedionate; and palladium complexes containing carbon monoxide, amines, nitrites, nitriles, phosphines or olefins, such as $PdCl_2(PhCN)_2$ and $PdCl_2(PPh_3)_2$. As used herein, the term "complexes" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes.

In various applications, it may be preferable to utilize palladium(II) salts of organic acids, including carboxylates with $C_{2-6}$ aliphatic carboxylic acids and palladium(II) salts of β-diketones. Palladium(II) acetate and palladium(II) 2,4-pentanedionate (also know as palladium(II) acetylacetonate) are generally most preferred. Mixtures of palladium materials are also contemplated.

The quantity of the at least one Group 8, 9, or 10 metal constituent is not particularly limited in the method of the present invention. In one embodiment the amount of Group 8, 9, or 10 metal source employed is sufficient to provide a molar ratio of metal to aromatic hydroxy compound in a range of between about 1:800 and about 1:1,000,000, in another embodiment a molar ratio of metal to aromatic hydroxy compound in a range of between about 1:4000 and about 1:1,000,000 moles, in still another embodiment a molar ratio of metal to aromatic hydroxy compound in a range of between about 1:40,000 and about 1:200,000, and in yet still another embodiment a molar ratio of metal to aromatic hydroxy compound in a range of between about 1:65,000 and about 1:100,000.

The catalyst system employed herein also contains at least one salt with anion selected from tetrafluoroborates, hexafluorophosphates, nitrates, carboxylates, benzoates, acetates, sulfates, tetraarylborates, arylsulfonates, alkylsulfonates, and halides. The cation portion of the salt can be at least one guanidinium salt or onium salt, including ammonium, phosphonium, or sulfonium salts that are substituted with organic residues. Illustrative examples of guanidinium salts include, but are not limited to, hexasubstituted guanidinium halides, such as hexaalkyl guanidinium halides, hexaaryl guanidinium halides, and hexasubstituted guanidinium halides containing mixtures of alkyl and aryl substituents each substituent group independently having a carbon number of 1 to 22; for example hexaalkylguanidinium chlorides or bromides. In one embodiment of the invention hexaethylguanidinium bromide is preferred. Illustrative examples of onium salts include, but are not limited to, tetraalkylammonium or tetraalkylphosphonium halides, sulfates, nitrates, p-tolylsulfonates, tetrafluoroborates, tetraarylborates, or hexafluorophosphates. In preferred embodiments the salts are halides such as the chlorides and bromides, particularly the bromides. Organic residues on the onium salts are typically include $C_{6-10}$ aryl, $C_{7-12}$ aralkyl, or $C_{1-20}$ alkyl, or combinations thereof. Preferred onium salts are tetraalkylammonium halides containing primary and/or secondary alkyl groups containing about 1–8 carbon atoms. In one embodiment onium salts comprise tetraethylammonium, tetramethylammonium, tetrabutylammonium, or methyltributylammonium cations. Tetraethylammonium bromide is particularly preferred.

In preferred embodiments, the cation portion of the salt may be chosen from alkali metal cations. Accordingly, a non-exclusive listing of preferred alkali metal salts includes those with anions listed hereinabove, such as lithium bromide, sodium chloride, sodium bromide, potassium bromide, and cesium bromide.

Mixtures of the aforementioned salts are also suitable for use in the invention. In one embodiment at least one salt is present in the mixture in an amount in a range of between about 1 mole and about 2000 moles per gram-atom of Group 8, 9, or 10 metal catalyst, in another embodiment in an amount in a range of between about 2 moles and about 1500 moles per gram-atom of Group 8, 9, or 10 metal catalyst, and in still another embodiment in an amount in a range of between about 5 moles and about 1000 moles per gram-atom of Group 8, 9, or 10 metal catalyst.

The catalyst system may include an effective amount of at least one activating organic solvent. Preferred activating organic solvents include polyethers; i.e., compounds containing two or more C—O—C linkages, for example as is disclosed in U.S. Pat. No. 6,114,564. The polyether used is preferably free from hydroxy groups to maximize its desired activity and avoid competition with the aromatic hydroxy compound in the carbonylation reaction. Preferred polyethers contain two or more (O—C—C) units.

The polyether may be aliphatic or mixed aliphatic-aromatic. As used in the identification of the polyether, the term "aliphatic" refers to the structures of hydrocarbon groups within the molecule, not to the overall structure of the molecule. Thus, "aliphatic polyether" includes heterocyclic polyether molecules containing aliphatic groups within their molecular structure. Suitable aliphatic polyethers include diethylene glycol dialkyl ethers such as diethylene glycol dimethyl ether (hereinafter "diglyme"), triethylene glycol dialkyl ethers such as triethylene glycol dimethyl ether (hereinafter "triglyme"), tetraethylene glycol dialkyl ethers such as tetraethylene glycol dimethyl ether (hereinafter "tetraglyme"), polyethylene glycol dialkyl ethers such as polyethylene glycol dimethyl ether and crown ethers such as 15-crown-5 (1,4,7,10,13-pentaoxacyclopentadecane) and 18-crown-6 (1,4,7,10,13,16-hexaoxacyclooctadecane). Illustrative mixed aliphatic-aromatic polyethers include diethylene glycol diphenyl ether and benzo-18-crown-6.

In alternative embodiments, the activating organic solvent can be a nitrile, for example as is disclosed in U.S. Pat. No. 6,172,254. Suitable nitrile solvents for the present method include $C_{2-8}$ aliphatic or $C_{7-10}$ aromatic mono- or dinitriles. Illustrative mononitriles include acetonitrile, propionitrile, and benzonitrile. Illustrative dinitriles include succinonitrile, adiponitrile, and benzodinitrile. Mononitriles are generally preferred; more specifically preferred is acetonitrile.

In further alternative embodiments, the activating organic solvent can be a carboxylic acid amide, for example as is disclosed in U.S. Pat. No. 6,180,812. Fully substituted amides (containing no NH groups including the amide nitrogen) are preferred. Aliphatic, aromatic or heterocyclic amides may be used. Illustrative amides are dimethylformamide, dimethylacetamide (hereinafter sometimes "DMA"), dimethylbenzamide and N-methylpyrrolidinone (NMP). Particularly preferred are NMP and DMA.

The activating organic solvent can be a sulfone, which may be aliphatic, aromatic or heterocyclic. Illustrative sulfones are dimethyl sulfone, diethyl sulfone, diphenyl sulfone and sulfolane (tetrahydrothiophene-1,1-dioxide). Of these, sulfolane is often preferred.

It is noted that the function of the activating organic solvent in the present invention is not that of an inert solvent. Rather, the activating organic solvent is an active catalyst component that improves the yield of or selectivity toward the aromatic carbonate. The role of the activating organic solvent is believed to be to increase the degree of dissociation and ionization of salt composition perhaps by forming a complex with the cationic portion of said component, although the invention is in no way dependent on this or any other theory of operation. The amount of activating organic solvent employed will be an amount effective to optimize aromatic carbonate formation, in general by increasing the yield of the desired aromatic carbonate as evidenced, for example, by an increase in "turnover number"; i.e., the number of moles of aromatic carbonate formed per gram-atom of the Group 8, 9, or 10 metal catalyst component present. In one embodiment this amount is in a range of between about 1% and about 60% by volume, in another embodiment in a range of between about 1% and about 25% by volume, in still another embodiment in a range of between about 2% and about 15% by volume, in still another embodiment in a range of between about 4% and about 12% by volume, and in yet still another embodiment in a range of between about 6% and about 8% by volume based on the total of aromatic hydroxy compound and activating organic solvent.

The amount of activating organic solvent may, however, typically depend to some extent on the salt composition and the complexing ability of the activating organic solvent employed. Crown ethers, for example, have a very high complexing tendency with metal cations. For example, 15-crown-5 complexes efficiently with sodium and 18-crown-6 with potassium. Such compounds may be used in amounts as low as an equimolar amount based on salt composition. Other compounds useful as activating organic solvent, such as straight chain polyethers (e.g., diglyme), may be optimally effective at much higher levels. The preferred proportion of any specific material used as activating organic solvent can be determined by simple experimentation.

There also can be used in combination with the Group 8, 9, or 10 metal constituent and catalyst system at least one quinone and aromatic diol formed by the reduction of said quinone or a mixture thereof. 1,4-Benzoquinone and hydroquinone are preferred. In addition, compounds such as 1,2-quinone and catechol, anthraquinone, 9,10-dihydroxyanthracene, and phenanthrenequinone also can be used. When present, the at least one quinone and aromatic diol formed by the reduction of said quinone or a mixture thereof may be present in one embodiment in an amount in a range of between about 10 moles and about 60 moles, and in another embodiment in an amount in a range of between about 25 moles and about 40 moles of quinone and/or reduction product thereof per gram-atom of Group 8, 9, or 10 metal catalyst.

In addition to the at least one Group 8, 9, or 10 metal constituent, there is present in the mixtures of the invention an effective amount of at least one metal co-catalyst (sometimes referred to hereinafter as inorganic co-catalyst or IOCC) containing a metal different from the at least one Group 8, 9, or 10 metal. Suitable metal co-catalysts include all those known in the art which promote formation of carbonate ester from aromatic hydroxy compound under reactive conditions in the presence of the at least one Group 8, 9, or 10 metal catalyst. Metal co-catalyst sources include elemental metals, metal compounds, and precursors thereof which may form catalytically active metal species under the reaction conditions, it being possible for use to be made of the metal in various degrees of oxidation. Metal co-catalysts may be initially soluble or partially soluble in the mixture, or initially insoluble as in supported- or polymer-bound metal co-catalyst species. Alternatively, metal co-catalysts may be initially insoluble in the mixture and form soluble metal co-catalyst species during the course of the reaction. Illustrative metal co-catalysts are disclosed in numerous patents and include, but are not limited to, either alone or in combination, lead, copper, titanium, cobalt, manganese, zinc, bismuth, zirconium, tungsten, chromium, nickel, iron, and lanthanide metals such as cerium, ytterbium and the like. Preferred metal co-catalysts include lead, copper, titanium, cobalt, manganese, and lanthanide metals such as cerium, either alone or in combination. In particularly preferred embodiments metal co-catalysts comprise compounds of lead, either used alone or in combination with at least one of a titanium source, copper source, or cerium source. In another particularly preferred embodiment metal co-catalysts comprise a mixture of at least one copper source and at least one titanium source.

The at least one metal co-catalyst can be introduced to the carbonylation reaction in various forms, including salts and complexes, such as tetradentate, pentadentate, hexadentate, heptadentate, octadentate, or nonadentate complexes. Illustrative forms may include oxides, halides, carboxylates (for example of carboxylic acids containing from 2–6 carbon atoms), diketones (including beta-diketones), nitrates, complexes containing carbon monoxide, olefins, amines, phosphines and halides, and the like. Suitable beta-diketones include those known in the art as ligands for the metal co-catalysts of the present invention. Examples include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). A metal co-catalyst may be used in its elemental form if sufficient reactive surface area can be provided.

A preferred class of metal co-catalysts comprises at least one lead source (sometimes referred to hereinafter as lead compound). A lead compound is preferably at least partially soluble in a liquid phase under the reaction conditions. Examples of such lead compounds include, but are not limited to, lead oxides, for example PbO, $Pb_3O_4$, and $PbO_2$; lead carboxylates, for example lead (II) acetate and lead (II) propionate; inorganic lead salts such as lead (II) nitrate and lead (II) sulfate; alkoxy and aryloxy lead compounds such as lead (II) methoxide, and lead (II) phenoxide; lead complexes such as lead (II) acetylacetonate and phthalocyanine lead, and organolead compounds (that is lead compounds having at least one lead-carbon bond) such as tetraethyl lead. Of these compounds, lead oxides and lead compounds represented by the formula $Pb(OR)_2$ wherein R is an aryl group having a carbon number from 6 to 10 are preferred. Mixtures of the aforementioned lead compounds are also contemplated.

Examples of titanium sources include inorganic titanium salts such as titanium (IV) bromide, titanium (IV) chloride; titanium alkoxides and aryloxides such as titanium (IV) methoxide, titanium (IV) ethoxide, titanium (IV) isopropoxide, titanium (IV) 2-ethylhexoxide, titanium (IV) butoxide, titanium (IV) 2-ethyl-1,3-hexanediolate, titanium (IV) (triethanolaminato)isopropoxide and titanium (IV) phenoxide; and titanium salts of β-diketones or β-ketoesters such as titanium (IV) diisopropoxide bis(acetylacetonate), titanium (IV) bis(ethyl acetoacetato)diisopropoxide, titanium (IV) oxide bis(2,4-pentanedionate) (or titanium (IV) oxide acetylacetonate). Mixtures of titanium compounds may also be employed. The preferred titanium sources are titanium (IV) alkoxides and aryloxides such as titanium (IV) butoxide and titanium (IV) phenoxide; and salts of β-diketones or β-ketoesters such as titanium (IV) oxide acetylacetonate and titanium (IV) bis(ethyl acetoacetato) diisopropoxide.

Examples of manganese sources (sometimes referred to hereinafter as manganese compound) include manganese halides, manganese chloride, manganese bromide, manganese nitrate, manganese carboxylates such as manganese (II) acetate, and manganese salts of β-diketones such as manganese (III) 2,4-pentanedionate and manganese (II) 2,4-pentanedionate (manganese (II) acetylacetonate). Mixtures of manganese compounds may also be employed. The preferred manganese compounds are manganese 2,4-pentanedionates.

Examples of copper sources (sometimes referred to hereinafter as copper compounds) are inorganic cupric or cuprous salts or copper complexes. Illustrative examples include, but are not limited to, copper (I) chloride, copper (I) bromide, copper (I) iodide; copper (II) chloride, copper (II) bromide, copper (II) iodide; copper carboxylates such as copper acetate, copper gluconate, and copper (II) 2-ethylhexanoate; copper (II) hydroxide, copper alkoxides and aryloxides; copper nitrate; and copper salts of β-diketones such as copper (II) bis(2,4-pentanedionate) (or copper (II) acetylacetonate). Mixtures of copper compounds may also be employed. The preferred copper compounds are 2,4-pentanedionates.

Lanthanide metals include cerium, praseodymium, neodymium, promethium, samarium, europium, gadolinium, terbium, dysprosium, holmium, erbium, thulium, ytterbium, and lutetium. Examples of lanthanide sources (sometimes referred to hereinafter as lanthanide compounds) include lanthanide carboxylates such as cerium acetate, and lanthanide salts of β-diketones such as lanthanide 2,4-pentanedionates (lanthanide acetylacetonates) or lanthanide hexafluoroacetylacetonates. Mixtures of lanthanide compounds may also be employed. In one embodiment preferred lanthanide compounds are cerium compounds including cerium carboxylates such as cerium acetate, and cerium salts of β-diketones such as cerium (III) 2,4-pentanedionate (cerium (III) acetylacetonate). Mixtures of cerium compounds may also be employed. The preferred cerium compounds are cerium 2,4-pentanedionates.

Examples of cobalt sources include cobalt (II) halide or carboxylate salts, such as cobalt chloride and cobalt acetate. Preferred cobalt sources include compounds of the type disclosed in U.S. Pat. No. 5,231,210; namely, complexes of cobalt(II) salts with organic compounds capable of forming complexes, especially pentadentate complexes, therewith. Illustrative organic compounds of this type are nitrogen-containing heterocyclic compounds including pyridines, bipyridines, terpyridines, quinolines, isoquinolines and biquinolines; aliphatic polyamines such as ethylenediamine and tetraalkylethylenediamines, such as tetramethylethylenediamine; crown ethers; aliphatic ethers; aromatic or aliphatic amine ethers such as cryptands; and Schiff bases. An especially preferred cobalt source is cobalt(II) salt of bis[3-(salicylalamino)-propyl]methylamine, sometimes known as "CoSMDPT".

IOCC's are included in the carbonylation catalyst system in effective amounts. In this context an "effective amount" is an amount of IOCC (or combination of IOCC's) that increases the number of moles of aromatic carbonate produced per mole of Group 8, 9, or 10 metal utilized; increases the number of moles of aromatic carbonate produced per mole of salt utilized; or increases selectivity toward aromatic carbonate production beyond that obtained in the absence of the IOCC (or combination of IOCC's). Effective amounts of an IOCC in a given application will depend on various factors, such as the identity of reactants and reaction conditions. In one embodiment at least one IOCC is present in an amount in a range of between about 0.1 gram-atoms of metal and about 200 gram-atoms of metal per gram-atom of the Group 8, 9, or 10 metal, in another embodiment in a range of between about 1 gram-atom of metal and about 150 gram-atoms of metal per gram-atom of the Group 8, 9, or 10 metal, and in still another embodiment in a range of between about 2 gram-atoms of metal and about 100 gram-atoms of metal per gram-atom of the Group 8, 9, or 10 metal. For example, when palladium is included in the reaction, the molar ratio of lead relative to palladium at the initiation of the reaction in one embodiment is in a range of between about 0.1 and about 150, in another embodiment in a range of between about 1 and about 100, and in still another embodiment in a range of between about 5 and about 100. In yet still another embodiment the molar ratio of lead relative to palladium at the initiation of the reaction is greater than about 17. In yet still another embodiment the molar ratio of lead relative to palladium at the initiation of the reaction is in a range of between about 25 and about 100.

At least one base may optionally be present in the mixture. Any effective bases or mixtures thereof, whether organic or inorganic may be used in the process of the invention. In preferred embodiments a base is used which is capable of generating the conjugate base of an aromatic hydroxy compound and not interfering with the function of any catalyst component. Illustrative examples of inorganic bases include, but are not limited to, alkali metal hydroxides and alkali metal carbonates, alkali metal carboxylates or other salts of weak acids or alkali metal salts of aromatic hydroxy compounds, for example alkali metal phenoxides. Obviously, the hydrates of alkali metal phenoxides can also be used in the process. An example of such a hydrate which may be mentioned is sodium phenoxide trihydrate. In general the use of hydrates and the concomitant addition of water to the mixture may lead, inter alia, to poorer conversion rates and decomposition of carbonates formed. Illustrative examples of organic bases include, but are not limited to, onium hydroxides, onium phenoxides, ammonium hydroxides, ammonium phenoxides, phosphonium hydroxides, phosphonium phenoxides, sulfonium hydroxides, sulfonium phenoxides, guanidinium hydroxides, guanidinium phenoxides, tertiary amines which bear as organic radicals $C_6$–$C_{10}$ aryl, $C_6$–$C_{12}$ aralkyl and/or $C_1$–$C_{20}$-alkyl or represent pyridine bases or hydrogenated pyridine bases; for example dimethylbutylamine, triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxy compound, particularly preferably an alkali metal salt of the aromatic hydroxy compound which is also to be converted to the organic carbonate. These alkali metal salts can be lithium salts, sodium salts, potassium salts, rubidium salts or cesium salts. Lithium phenoxide, sodium phenoxide and potassium phenoxide are preferably used; sodium phenoxide is particularly preferred.

A base may be added as a pure compound or as a precursor compound, such as addition of an alkali metal-comprising base as a precursor for an alkali metal salt of the aromatic hydroxy compound which is also to be converted to the organic carbonate. Illustrative alkali metal-comprising bases include, but are not limited to, sodium hydroxide, and sodium salts of weak acids such as sodium carboxylates, sodium acetate, and sodium acetylacetonate. A base may be added to the mixture in any convenient form, such as in solid form or as a liquid or a melt, either in neat form or in a solution. In a further embodiment of the invention, the base is added to the mixture as a solution which contains an amount in a range of between about 0.1% and about 80% by weight of base, in another embodiment an amount in a range of between about 0.5% and about 65% by weight of base, and in still another embodiment an amount in a range of between about 1% and about 50% by weight of base. The solvents which may optionally be used in this context include aromatic hydroxy compounds, such as the aromatic hydroxy compound to be reacted, particularly phenol, and inert solvents. Examples of solvents which may be mentioned are dimethylacetamide, N-methylpyrrolidinone, dioxane, tetramethylurea, halogenated hydrocarbons (e.g. chlorobenzene or dichlorobenzene) and ethers, such as tetraethylene glycol dimethyl ether. The solvents may be used alone or in any combination with each other.

A base, if used, is added in an amount independent of the stoichiometry. The ratio of base to Group 8, 9, or 10 metal is preferably chosen in such a way that at least one base is present in an amount in a range of between about 0.1 molar equivalent and about 2500 molar equivalents of base based on Group 8, 9, or 10 metal, in another embodiment in a range of between about 5 molar equivalents and about 1500 molar equivalents of base based on Group 8, 9, or 10 metal, in still another embodiment in a range of between about 50 molar equivalents and about 1000 molar equivalents of base based on Group 8, 9, or 10 metal, and in still another embodiment in a range of between about 100 molar equivalents and about 400 molar equivalents of base based on Group 8, 9, or 10 metal.

The carbonylation reaction can be carried out under batch conditions or under continuous or semi-continuous conditions in reactor systems comprising one or more reaction vessels. Reaction vessels suitable for use in the method according to the invention with either homogeneous or heterogeneous catalysts include stirrer vessels, autoclaves and bubble columns, it being possible for these to be employed as individual reactors or as a cascade. In a cascade 2 to 15, preferably 2 to 10, and particularly preferably 2 to 5, reactors may be connected in series.

The reaction gases are not subject to special purity requirements but care must be taken to ensure that no catalyst poisons such as sulfur or compounds thereof are introduced. In a preferred embodiment pure carbon monoxide and pure oxygen are used. Carbon monoxide and oxygen can be introduced as a mixture or in a preferred embodiment, carbon monoxide and oxygen may be added independently of each other. When a reactor cascade is used instead of an individual reactor, the separate oxygen addition preferably proceeds in such a way that the optimal oxygen concentration is ensured in each of the reactors.

The compositions of the reaction gases carbon monoxide and oxygen can be varied in broad concentration ranges. In one embodiment a molar ratio of carbon monoxide:oxygen (normalized on carbon monoxide) is employed in a range of between about 1:0.001 and about 1:1, in another embodiment in a range of between about 1:0.01 and about 1:0.5, and in still another embodiment in a range of between about 1:0.02 and about 1:0.3. A total pressure is employed in one embodiment in the range of between about 0.1013 megapascals and about 50.6625 megapascals, in another embodiment in a range of between about 0.3447 megapascals and about 25.33 megapascals, in still another embodiment in a range of between about 1.013 megapascals and about 17.2369 megapascals, and in still another embodiment in a range of between about 1.013 megapascals and about 15.1987 megapascals.

The carbon monoxide may be high-purity carbon monoxide or carbon monoxide diluted with another gas which has no negative effects on the reaction, such as nitrogen, noble gases, or argon. The oxygen used in the present invention may be high purity oxygen, air, or oxygen diluted with any other gas which has no negative effects on the reaction, such as nitrogen, noble gases, or argon. The concentration of inert gas in the reaction gas may be in one embodiment an amount in a range of between 0 and about 60 volume %, in another embodiment an amount in a range of between 0 and about 20 volume %, and in still another embodiment an amount in a range of between 0 and about 5 volume %. The concentration of 0 volume % represents the special case of the preferred state which is free of inert gas.

In a further preferred embodiment carbon monoxide and oxygen may be added independently of each other. The oxygen addition, in this case, can take place, if desired, together with inert gas. When a reactor cascade is used instead of an individual reactor, the separate oxygen addition preferably proceeds in such a way that the optimal oxygen concentration is ensured in each of the reactors.

The reaction gas, comprising carbon monoxide, oxygen and, optionally, an inert gas, may be introduced at a rate in one embodiment in a range of between about 1 liter and about 100,000 liters (S.T.P.) per liter of reaction solution per hour, in another embodiment in a range of between about 5 liters and about 50,000 liters (S.T.P.) per liter of reaction solution per hour, and in still another embodiment in a range of between about 10 liters and about 10,000 liters (S.T.P.) per liter of reaction solution per hour.

Provision may be made for including a drying agent or a drying process step in the overall reaction method. Higher catalyst turnover numbers are typically obtained if water is removed from the reaction mixture during the reaction. For example, drying agents, typically molecular sieves, may be present in the reaction vessel as described, for example, in U.S. Pat. Nos. 5,399,734 and 6,191,299, both assigned to the assignee of the present invention. In another embodiment, a drying process step is included in the reaction method, such as a continuous method, for example, in U.S. Pat. Nos. 5,498,742 and 5,625,091, and in 5,917,078 which is assigned to the assignee of the present invention.

In one embodiment ultimate reaction temperatures above about 50° C. are employed, while in another embodiment ultimate reaction temperatures above about 70° C. are employed, and in still another embodiment ultimate reaction temperatures above about 80° C. are employed. In various embodiments ultimate reaction temperatures are in a range of between about 50° C. and about 150° C. In other embodiments ultimate reaction temperatures above about 90° C. are employed, with ultimate reaction temperatures in a range of between about 90° C. and about 110° C. being employed in still other embodiments. Gas sparging or mixing can be used to aid the reaction.

In one embodiment the present invention comprises an effective start-up procedure for a carbonylation reaction. The effective start-up procedure typically avoids rapid inactivation of carbonylation catalyst system and results in high yields of aromatic carbonate. In one particular embodiment a start-up procedure is applied to a carbonylation reaction mixture comprising catalyst components and aromatic hydroxy compound which is initially at a temperature sufficient to keep the mixture molten, typically a temperature in a range between about room temperature and about 50° C., depending upon such factors as mixture composition and melting point of aromatic hydroxy compound present. In general a start-up procedure is a series of process steps which is applied before a carbonylation reaction mixture has achieved equilibrium operating conditions. More particularly, a start-up procedure is a series of process steps required to transition a carbonylation reaction mixture from ambient pressure and a temperature no higher than about that necessary to keep the mixture molten to the elevated pressure under a gas mixture comprising carbon monoxide and oxygen and the elevated temperature which define the optimum range of equilibrium operating conditions.

Thus, in one embodiment the present invention is a method for producing aromatic carbonates which comprises the steps of:

(i) contacting at a temperature sufficient to keep the mixture molten at least one aromatic hydroxy compound with a catalyst composition comprising the following and any reaction products thereof:
  (A) at least one Group 8, 9, or 10 metal or a compound thereof;
  (B) at least one salt;
  (C) at least one metal co-catalyst; and
  (D) optionally, at least one activating solvent;
(ii) optionally heating the mixture at atmospheric pressure to a temperature above that sufficient to keep the mixture molten;
(iii) pressurizing the mixture with carbon monoxide;
(iv) optionally heating the mixture under pressure of carbon monoxide to a temperature above that sufficient to keep the mixture molten;
(v) optionally maintaining the mixture under pressure of carbon monoxide for a time period;
(vi) introducing oxygen to the mixture to a desired concentration of oxygen in carbon monoxide;
(vii) starting gas flow to the mixture at a desired concentration of oxygen and carbon monoxide;
(viii) optionally maintaining gas flow for a time period at less than a desired ultimate temperature for the mixture; and
(ix) optionally heating the mixture to a desired ultimate temperature under flow of gases.

Step (i) of the method comprises contacting at a temperature sufficient to keep the mixture molten at least one aromatic hydroxy compound with a catalyst composition. The catalyst composition may be provided in its entirety at this time or additional catalyst components or aromatic hydroxy compound, or both may be added during or after the start-up procedure. In one embodiment the catalyst composition is present initially in an amount effective for carbonylation of aromatic hydroxy compound.

Step (ii) of the method comprises optionally heating the mixture at atmospheric pressure to a temperature above that sufficient to keep the mixture molten. Whether the mixture is heated or not, the temperature that is attained thereby, and the time of heating may be determined by various factors, such as the application of and the parameters associated with other steps of the method. In one preferred embodiment the mixture is not heated above about that temperature sufficient to keep the mixture molten before step (iii) is applied. If heat is applied, the temperature attained in step (ii) is no higher than about 90° C. in one embodiment, and in another embodiment is in a range between about that temperature required to keep the mixture molten and about 90° C. In still another embodiment the mixture is heated to a temperature in a range of between about 55° C. and about 90° C., in another embodiment to a temperature in a range of between about 72° C. and about 90° C., and in still another embodiment to a temperature in a range of between about 80° C. and about 89° C. In still other embodiments the mixture is heated to a temperature no higher than about 72° C., and in yet still other embodiments to a temperature in a range between about 60° C. and about 72° C. When heat is applied to a mixture at atmospheric pressure to provide a temperature above that temperature required to keep the mixture molten, it may be applied for a time period which in one embodiment is in a range of between about 1 minute and about 60 minutes, in another embodiment in a range of between about 2 minutes and about 45 minutes, and in still another embodiment in a range of between about 3 minutes and about 35 minutes.

Step (iii) of the method comprises pressurizing the mixture with carbon monoxide. Pressurization of the mixture typically requires about 10 seconds to about 24 hours depending upon such factors as the size of the reactor or reactors. In typical embodiments pressures are in a range of between about 0.1 megapascals and about 50 megapascals, in another embodiment in a range of between about 0.3 megapascals and about 25 megapascals, in still another embodiment in a range of between about 1 megapascals and about 17 megapascals, and in still another embodiment in a range of between about 1 megapascals and about 15 megapascals. In yet still another embodiment pressures are in a range of between about 6 megapascals and about 10 megapascals.

Step (iv) of the method comprises optionally heating the mixture under pressure of carbon monoxide to a temperature above that sufficient to keep the mixture molten. Whether the mixture is heated or not in this step, and also the temperature that is attained thereby may be determined by various factors, such as the application of and the parameters associated with other steps of the method. If optional step (ii) has been applied, then the mixture may be heated in optional step (iv) to a temperature above that attained through heating in optional step (ii). Preferably the temperature of the mixture attained in optional step (iv) is in a range between that temperature sufficient to keep the mixture molten and a desired ultimate reaction temperature. In one embodiment the mixture is heated in step (iv) to a desired ultimate reaction temperature.

Step (v) of the method comprises optionally maintaining the mixture under pressure of carbon monoxide over a period of time. Whether this time period is applied or not may be determined by various factors, such as the application of and the parameters associated with other steps of the method. The time period may be in a range between 0 minutes and about 40 minutes. In one embodiment the time period is less than 5 minutes and in another embodiment 0 minutes. In another embodiment the time period is in a range of between about 5 minutes and about 40 minutes, in still another embodiment in a range of between about 10 minutes and about 35 minutes, and in yet still another embodiment in a range of between about 15 minutes and about 30 minutes.

Step (vi) of the method comprises introducing oxygen to the mixture to a desired concentration of oxygen in carbon monoxide. Oxygen may be introduced by any convenient method, such as in a mixture with carbon monoxide pre-mixed before introduction to the mixture, or via a separate inlet tube as oxygen not mixed with carbon monoxide. Concentrations of oxygen entering a reactor based on carbon monoxide are in one embodiment in a range of between about 4 molar % and about 10 molar %, and in another embodiment in a range of between about 5.5 molar % and about 9.5 molar %. When optional step (v) has been applied and the mixture is held for a time under pressure of carbon monoxide, then the concentration of oxygen introduced in step (vi) is in one embodiment greater than about 8 molar % based on carbon monoxide and in another embodiment in a range of between about 8 molar % and about 10 molar % based on carbon monoxide.

Step (vii) of the method comprises starting gas flow to the mixture at a desired concentration of oxygen and carbon monoxide. Under flow conditions the concentration of oxygen exiting a reactor is lower than the concentration of oxygen entering a reactor. The concentration of oxygen exiting a reactor is typically in a range of between about 2% and about 8%, and more typically in a range of between about 6.5% and about 7.5% based on carbon monoxide. Step (viii) of the method comprises optionally maintaining gas flow for a time period at less than a desired ultimate temperature for the mixture. Whether this time period is applied or not may be determined by various factors, such as the application of and the parameters associated with other steps of the method. When this time period of step (viii) is applied, it is in one embodiment for a period in a range of between about 5 minutes and about 30 minutes, and in another embodiment for a period in a range of between about 10 minutes and about 20 minutes.

Step (ix) of the method comprises optionally heating the mixture to a desired ultimate temperature under flow of gases. Optional step (ix) is applied when the mixture has not already been heated to a desired ultimate temperature in optional steps (ii) or (iv). The time required to heat the mixture to a desired ultimate temperature is in one embodiment in a range of between about 5 minutes and about 24 hours, in another embodiment in a range of between about 5 minutes and about 30 minutes, and in still another embodiment in a range of between about 5 minutes and about 15 minutes depending upon such factors as the size of the reactor or reactors. At a desired ultimate reaction temperature under flow of reaction gases the reaction may be allowed to proceed for a desired period to produce aromatic carbonate. It should be recognized that more than one ultimate reaction temperature may be desired in any particular carbonylation reaction depending upon such factors as inclusion of at least one drying process step and addition of additional catalyst components or substrate or both. Thus, an ultimate reaction temperature may be varied following a start-up procedure.

In another embodiment, the invention provides a method for producing aromatic carbonate from a mixture comprising an aromatic hydroxy compound, which comprises the steps of:

(x) maintaining the mixture at a temperature at least sufficient to keep the mixture molten;

(xi) introducing oxygen and carbon monoxide to the mixture to a desired pressure;

(xii) starting gas flow to the mixture at a desired concentration of oxygen and carbon monoxide;

(xiii) heating the mixture to a temperature in a range between that sufficient to keep the mixture molten and a desired ultimate temperature; and (xiv) contacting the mixture with one or more mixtures comprising aromatic hydroxy compound and one or more catalyst components comprising the following and any reaction products thereof:

(A) at least one Group 8, 9, or 10 metal or a compound thereof;

(B) at least one salt;

(C) at least one metal co-catalyst; and (D) optionally, at least one activating solvent.

Step (x) of the method comprises maintaining the mixture at a temperature at least sufficient to keep the mixture molten, typically a temperature in a range of between about room temperature and about 50° C. Such temperature may readily be determined and depends upon such factors as the melting point of the aromatic hydroxy compound present and whether any other species are present in the mixture, such as, for example, at least one activating solvent. In one embodiment the mixture consists essentially of aromatic hydroxy compound and the mixture is maintained above the melting point of said aromatic hydroxy compound.

Step (xi) of the method comprises introducing oxygen and carbon monoxide to the mixture to a desired pressure. Either carbon monoxide may be introduced first, or oxygen may be introduced first, or oxygen and carbon monoxide may be introduced as a mixture. In one embodiment oxygen is introduced at a desired concentration in a mixture with carbon monoxide. The pressure attained may be a desired ultimate pressure or less than a desired ultimate pressure. In one embodiment the pressure attained is a desired ultimate pressure.

Step (xii) of the method comprises starting gas flow to the mixture at a desired concentration of oxygen and carbon monoxide. Typically gas flow proceeds at a desired ultimate pressure. Step (xiii) of the method comprises heating the mixture to a temperature in a range between that sufficient to keep the mixture molten and a desired ultimate temperature. In one embodiment the mixture is heated to a desired ultimate temperature. In various embodiments the order of steps may comprise employing step (xiii) before either step (xi) or step (xii).

Step (xiv) of the method comprises contacting the mixture with one or more mixtures comprising aromatic hydroxy compound and one or more catalyst components. In one embodiment the mixture is contacted with a mixture of aromatic hydroxy compound containing essentially all the catalyst components. In another embodiment the mixture is contacted with two or more mixtures of aromatic hydroxy compound each containing at least one catalyst component. In another embodiment additional aromatic hydroxy compound may be added to the mixture as a separate stream along with any mixture of aromatic hydroxy compound containing at least one catalyst component. In still another embodiment at least one catalyst component is added not as a mixture with aromatic hydroxy compound. An illustrative example includes adding at least one activating solvent not as a mixture with aromatic hydroxy compound. In another embodiment the carbonylation process is continuous or semi-continuous, and a liquid stream is removed from the carbonylation reaction mixture for further processing comprising such steps as drying and removal of at least a portion of carbonylation reaction product. At least a portion of said liquid stream after further processing may be returned to the reaction mixture.

Applying steps of a controlled start-up procedure renders a carbonylation catalyst system more effective for producing high yields of aromatic carbonate. Although the present invention is not limited by theory of operation, it is believed that applying steps of a controlled start-up procedure minimizes catalyst inactivation. Catalyst inactivation during start-up procedure may result from chemical reduction of the Group 8, 9, or 10 metal catalyst component and association of the reduced metal particles into agglomerates which may have surface area too low to permit ready oxidation back to active catalyst species in the presence of oxygen. In particular it is believed that a high concentration of carbon monoxide and also possibly high temperature in the absence of sufficient oxygen may be detrimental to catalyst activity and lifetime depending upon such factors as catalyst composition. However, the invention is not dependent on this or any other theory of operation.

In one embodiment of the invention a carbonylation reaction mixture is exposed to an atmosphere comprising at least about 8 molar % oxygen before the mixture is heated to a temperature above about 90° C.

In a preferred embodiment of the invention optional step (ii) of the method is applied and a carbonylation reaction mixture is heated to a temperature in a range of between about 80° C. and about 89° C.; optional step (iv) is not applied; and optional step (v) is applied, wherein the mixture is held under pressure of carbon monoxide for a time before introducing oxygen to the mixture at a concentration of greater than about 8 molar % based on carbon monoxide; then optional step (viii) is applied wherein gas flow is maintained for a time period at less than a desired ultimate reaction temperature for the mixture; and finally optional step (ix) is applied wherein the mixture is heated to a desired ultimate temperature under flow of gases.

In another preferred embodiment of the invention optional steps (ii), (viii), and (ix) of the method are not applied, whereas optional step (iv) is applied, wherein a carbonylation reaction mixture is heated to a desired ultimate reaction temperature; and optional step (v) is also applied, wherein the mixture is held under pressure of carbon monoxide for a time before introducing oxygen to the mixture at a concentration of greater than about 8 molar % based on carbon monoxide.

In still another preferred embodiment of the invention optional step (ii) of the method is applied and a carbonylation reaction mixture is heated to a temperature no higher than about 72° C.; optional steps (iv), (v), and (viii) are not applied; oxygen is introduced to the mixture in step (vi) at a concentration in a range of between about 5.5 molar % and about 9.5 molar % based on carbon monoxide; and optional step (ix) is applied wherein the mixture is heated to a desired ultimate temperature under flow of gases.

In yet still another preferred embodiment of the invention optional step (ii) of the method is applied and a carbonylation reaction mixture is heated to a temperature no higher than about 72° C.; optional step (iv) is not applied; optional step (v) is applied wherein the mixture is held under pressure of carbon monoxide for a time before introducing oxygen to the mixture; oxygen is introduced to the mixture in step (vi) at a concentration greater than about 8 molar % based on carbon monoxide; optional step (viii) is not applied; and optional step (ix) is applied wherein the mixture is heated to a desired ultimate temperature under flow of gases.

In still another preferred embodiment of the invention optional steps (ii) and (viii) of the method are not applied, whereas optional step (iv) is applied, wherein a carbonylation reaction mixture is heated to a temperature above that sufficient to keep the mixture molten and below a desired ultimate reaction temperature; optional step (v) is also applied, wherein the mixture is held under pressure of carbon monoxide for a time before introducing oxygen to the mixture at a concentration of greater than about 8 molar % based on carbon monoxide; and optional step (ix) is applied wherein the mixture is heated to a desired ultimate temperature under flow of gases.

The following examples are included to provide additional guidance to those skilled in the art in practicing the claimed invention. While some of the examples are illustrative of various embodiments of the claimed invention, others are comparative. The examples provided are merely representative of the work that contributes to the teaching of the present application. Accordingly, these examples are not intended to limit the invention, as defined in the appended claims, in any manner.

As discussed above, the economics of aromatic carbonate production is dependent on the number of moles of aromatic carbonate produced per mole of Group 8, 9, or 10 metal utilized. In the following examples, the aromatic carbonate produced is diphenylcarbonate (DPC) and the Group 8, 9, or 10 metal utilized is palladium.

EXAMPLES 1–11

Catalyst system activity was studied using a constant composition gas flow reactor. In each example the reactor was initially charged with 60 grams (g) phenol, 5 milligrams (mg) palladium acetylacetonate, 52 mg lead (II) oxide, and 3.2 g hexaethylguanidinium bromide and treated under pressure with a gas mixture using protocols described below. Gas flow for each example was in a range of between about 320 milliliters per minute and about 330 milliliters per minute with the exception of Example 8 which had a gas flow of about 160 milliliters per minute. The ultimate reaction temperature in each example was 100° C. Reaction mixtures were analyzed by high performance liquid chromatography (HPLC) after 1.5 hours at final reaction temperature. Results are shown in Table 1. Megapascals are abbreviated mPa. Examples prefaced with "C" are comparative examples.

TABLE 1

| Example | Heat at atmos. press.? optional step (ii) | Temp./Time at atmos. press. | Heat under CO press.? optional step (iv) | Batch CO-only period? optional step (v) | Press./Temp./ Time of CO-only period | % Oxygen in CO | Gas flow with CO/oxygen at less than rx. temp.? optional step (viii) | Temp./Time of gas flow with CO/oxygen | Heat to an ultimate rx. temp.? optional step (ix) | Wt. % DPC at 1.5 hrs. |
|---|---|---|---|---|---|---|---|---|---|---|
| 1 | Yes | 80–89° C. 8 min. | No | Yes | 8.3 mPa/80° C./ 15 min. | 9.1 | Yes | 80° C. 15 min. | Yes | 16.4 |
| C2 | Yes | 80–89° C. 7 min. | No | Yes | 8.7 mPa/80° C./ 15 min. | 4.5–6.0 | No | — | Yes | 4.7 |
| C3 | Yes | 80–88° C. 30 min. | No | Yes | 8.5 mPa/80° C./ 15 min. | 6 | No | — | Yes | 2.0 |
| C4 | Yes | 80–85° C. 30 min. | No | No | — | 6 | No | — | Yes | 1.4 |
| C5 | Yes | 100–104° C. 30 min. | No | No | — | 9.1 | No | — | No | 1.5 |
| 6 | No | — | Yes | Yes | 8.3 mPa/100° C./ 30 min. | 9.1 | No | — | No | 14.2 |
| 7 | Yes | 60–72° C. 30 min. | No | No | — | 6 | No | — | Yes | 16.1 |
| 8 | Yes | 60–72° C. 30 min. | No | No | — | 6 | No | — | Yes | 15.5 |
| 9 | Yes | 60–72° C. 30 min. | No | Yes | 8.3 mPa/60° C./ 15 min. | 9.1 | No | — | Yes | 16.2 |
| C10 | Yes | 60–72° C. 30 min. | No | Yes | 8.5 mPa/60° C./ 15 min. | 6.0–7.5 | No | — | Yes | 8.8 |
| 11 | No | — | No | No | — | 9.1 | No | — | Yes | 17.5 |

Example 1 shows the beneficial effect of including optional step (ii) of the method and heating a carbonylation reaction mixture to a temperature in a range between about 80° C. and 89° C.; and also applying optional step (v), wherein the mixture is held under pressure of carbon monoxide for a time before introducing oxygen to the mixture at a concentration of greater than about 8 molar % based on carbon monoxide; followed by applying optional step (viii) wherein gas flow is maintained for a time period at less than a desired ultimate reaction temperature for the mixture; and finally applying optional step (ix), wherein the mixture is heated to a desired ultimate temperature. Comparative Examples 2 and 3 are similar to Example 1, and show the detrimental effect on product yield of adding oxygen at a concentration of less than about 8 molar % when the mixture has been previously heated in optional step (ii) to a temperature greater than about 72° C. for various periods. Comparative Example 4 is also similar to Example 1, and shows the detrimental effect on product yield of adding oxygen at a concentration of less than about 8 molar % when the mixture has been previously heated in optional step (ii) to a temperature greater than about 72° C., even when optional step (v) is omitted. The absence of optional step (viii) in comparative Examples 2, 3, and 4 is not believed to be of consequence to the conclusions under these conditions. Comparative Example 5 shows the detrimental effect of heating the mixture to a temperature above 90° C. in optional step (ii) even when greater than 8 molar % oxygen is subsequently added.

Example 6 shows the beneficial effect on product yield under conditions wherein optional steps (ii), (viii), and (ix) are omitted; optional step (iv) is applied wherein a carbonylation reaction mixture is heated to a desired ultimate reaction temperature; and optional step (v) is also applied, wherein the mixture is held under pressure of carbon monoxide for a time before introducing oxygen to the mixture at a concentration of greater than about 8 molar % based on carbon monoxide.

Examples 7, 8, and 9 show the beneficial effect on product yield of including optional step (ii) of the method wherein a carbonylation reaction mixture is heated to a temperature at or less than about 72° C. Under these conditions, when optional step (v) is not applied (Examples 7 and 8), then little difference is seen whether oxygen is introduced at a concentration of greater than about 8 molar % based on carbon monoxide or not. Under similar conditions, when optional step (v) is applied (Example 9), then a beneficial effect is seen when oxygen is introduced at a concentration of greater than about 8 molar % based on carbon monoxide. Comparative Example 10 is similar to Example 9, and shows the detrimental effect on product yield of adding oxygen at a concentration of less than about 8 molar % when optional step (v) is included, even when the mixture has been previously heated in optional step (ii) to a temperature at or less than about 72° C.

Example 11 shows that a high yield of DPC may be obtained when optional steps (ii), (iv), (v), and (viii) are omitted and the carbonylation reaction mixture is not exposed to excessive heat or concentration of carbon monoxide in the absence of sufficient oxygen.

EXAMPLES 12–15

Carbonylation reactions were run as described in Examples 1–11 except that different catalyst systems were used. In Examples 12–13 the reactor was initially charged with 50.72 g phenol, 0.3 g benzophenone (added as internal standard), 3.75 milligrams (mg) palladium acetylacetonate, 160 mg lead (II) oxide, 6.5 mg titanium (IV) oxide acetylacetonate, 444 mg sodium bromide, and 2.51 milliliters tetraglyme, and treated under pressure with a gas mixture using protocols described below. In Examples 14–15 the reactor was initially charged with 47.48 g phenol, 0.3 g benzophenone (added as internal standard), 2.8 milligrams (mg) palladium acetylacetonate, 121 mg lead (II) oxide, 4.9 mg titanium (IV) oxide acetylacetonate, 544 mg sodium bromide, 46.9 mg sodium hydroxide, and 2.85 milliliters tetraglyme, and treated under pressure with a gas mixture using protocols described below. The ultimate reaction temperature in each example was 100° C. Reaction mixtures were analyzed by high performance liquid chromatography (HPLC) after 1.5 hours at final reaction temperature. Results are shown in Table 2. Megapascals are abbreviated mPa.

TABLE 2

| Example | Heat at atmos. press.? optional step (ii) | Temp./Time at atmos. press. | Heat under CO press.? optional step (iv) | Batch CO-only period? optional step (v) | Press./Temp./ Time of CO-only period | % Oxygen in CO | Gas flow with CO/oxygen at less than rx. temp.? optional step (viii) | Temp./Time of gas flow with CO/oxygen | Heat to an ultimate rx. temp.? optional step (ix) | Wt. % DPC at 1.5 hrs. |
|---|---|---|---|---|---|---|---|---|---|---|
| 12 | No | — | Yes | Yes | 8.3 mPa/80° C./ 15 min. | 9.1 | No | — | Yes | 15.9 |
| 13 | No | — | No | No | — | 9.1 | No | — | Yes | 15.7 |
| 14 | No | — | Yes | Yes | 8.5 mPa/80° C./ 15 min. | 9.1 | No | — | Yes | 18.0 |
| 15 | No | — | No | No | — | 9.1 | No | — | Yes | 17.5 |

Example 12–15 employ a different catalyst system from Examples 1–11 and show that embodiments of the invention are generally applicable irregardless of catalyst system employed. Example 12 and 14 show that a high yield of DPC may be obtained when optional steps (ii) and (viii) are omitted; optional step (iv) is applied wherein a carbonylation reaction mixture is heated under pressure of carbon monoxide to a temperature above that sufficient to keep the mixture molten and below a desired ultimate reaction temperature; optional step (v) is applied, wherein the mixture is held under pressure of carbon monoxide for a time before introducing oxygen to the mixture at a concentration of greater than about 8 molar % based on carbon monoxide; and optional step (ix) is applied wherein a carbonylation reaction mixture is heated to a desired ultimate reaction temperature under flow of gases.

Examples 13 and 15 show that a high yield of DPC may be obtained when optional steps (ii), (iv), (v), and (viii) are omitted and the carbonylation reaction mixture is not exposed to excessive heat or concentration of carbon monoxide in the absence of sufficient oxygen.

While the invention has been illustrated and described as embodied in a method for producing aromatic carbonates, it is not intended to be limited to the details shown, since various modifications and substitutions can be made without departing in any way from the spirit of the present invention. For example, additional effective IOCC compounds and different halide sources can be used in the reaction. As such, further modifications and equivalents of the invention herein disclosed may occur to persons skilled in the art using no more than routine experimentation, and all such modifications and equivalents are believed to be within the spirit and scope of the invention as defined by the following claims. All of the U.S. Patents mentioned herein are incorporated herein by reference.

What is claimed is:

1. A method for producing diphenyl carbonate which comprises the steps of:
   (i) contacting phenol at a temperature sufficient to keep the mixture molten with a catalyst composition consisting essentially of the following and any reaction products thereof:
      (A) at least one palladium source;
      (B) at least one tetrafluoroborate, hexafluorophosphate, tetraarylborate, arylsulfonate, sulfate, nitrate, carboxylate, acetate, benzoate, halide, chloride, or bromide salt with cation selected from the group consisting of guanidinium, ammonium, phosphonium, sulfonium, and alkali metal;
      (C) at least one metal co-catalyst with metal selected from the group consisting of lead, cobalt, copper, titanium, manganese, cerium, and mixtures thereof; and
      (D) optionally, at least one activating solvent;
   (ii) heating the mixture at atmospheric pressure to a temperature in a range of between about 72° C. and about 90° C.;
   (iii) pressurizing the mixture with carbon monoxide;
   (v) maintaining the mixture under pressure of carbon monoxide for a time period;
   (vi) introducing oxygen to the mixture at a concentration of greater than about 8 molar % based on carbon monoxide;
   (vii) starting gas flow to the mixture at a desired concentration of oxygen and carbon monoxide;
   (viii) maintaining gas flow for a time period at less than a desired ultimate temperature for the mixture; and
   (ix) heating the mixture to a desired ultimate temperature wider flow of gases.

2. A method for producing diphenyl carbonate which comprises the steps of:
   (i) contacting phenol at a temperature between about 72° C. and about 90° C. with a catalyst composition consisting essentially of the following and any reaction products thereof;
      (A) at least one palladium source;
      (B) at least one tetrafluoroborate, hexafluorophosphate, tetraarylborate, arylsulfonate, sulfate, nitrate, carboxylate, acetate, benzoate, halide, chloride, or bromide salt with cation-selected from the group consisting of guanidinium, ammonium, phosphonium, sulfonium, and alkali metal;
      (C) at least one metal co-catalyst with metal selected from the group consisting of lead, cobalt, copper, titanium, manganese, cerium, and mixtures thereof; and
      (D) optionally, at least one activating solvent;
   (iii) pressurizing the mixture with carbon monoxide;
   (iv) heating the mixture under pressure of carbon monoxide to a desired ultimate temperature;
   (v) maintaining the mixture under pressure of carbon monoxide for a time period;
   (vi) introducing oxygen to the mixture at a concentration of greater than about 8 molar % based on carbon monoxide; and
   (vii) starting gas flow to the mixture am a desired concentration of oxygen and carbon monoxide.

3. A method for producing diphenyl carbonate which comprises the steps of:

(i) contacting phenol at a temperature sufficient to keep the mixture molten with a catalyst composition consisting essentially of the following and any reaction products thereof:
  (A) at least one palladium source;
  (B) at least one tetrafluoroborate, hexafluorophosphate, tetraarylborate, arylsulfonate, sulfate, nitrate, carboxylate, acetate, benzoate, halide, chloride, or bromide salt with cation selected from the group consisting of guanidinium, ammonium, phosphonium, sulfonium, and alkali metal;
  (C) at least one metal co-catalyst with metal selected from the group consisting of lead, cobalt, copper, titanium, manganese, cerium, and mixtures thereof; and
  (D) optionally, at least one activating solvent;

(ii) heating the mixture at atmospheric pressure to a temperature in a range of between about 72° C. and about 90° C.;

(iii) pressurizing the mixture with carbon monoxide;

(vi) introducing oxygen to the mixture at a concentration of greater than about 8 molar % based on carbon monoxide with the proviso that the solvent for the reaction mixture before the introduction of oxygen consists of the aromatic hydroxy compound;

(vii) starting gas flow to the mixture at a desired concentration of oxygen and carbon monoxide; and (ix) heating the mixture to a desired ultimate temperature under flow of gases.

* * * * *